US012716084B2

(12) United States Patent
Gritsch et al.

(10) Patent No.: US 12,716,084 B2
(45) Date of Patent: Aug. 25, 2026

(54) HEPARIN-INSENSITIVE ASSAY FOR FACTOR XIA

(71) Applicant: Takeda Pharmaceutical Company Limited, Osaka (JP)

(72) Inventors: Herbert Gritsch, Vienna (AT); Magdalena Schlager, Vienna (AT); Alfred Weber, Vienna (AT)

(73) Assignee: Takeda Pharmaceutical Company Limited, Osaka (JP)

( * ) Notice: Subject to any disclaimer, the term of this patent is extended or adjusted under 35 U.S.C. 154(b) by 920 days.

(21) Appl. No.: 17/761,548

(22) PCT Filed: Oct. 9, 2020

(86) PCT No.: PCT/US2020/054881
§ 371 (c)(1),
(2) Date: Mar. 17, 2022

(87) PCT Pub. No.: WO2021/072137
PCT Pub. Date: Apr. 15, 2021

(65) Prior Publication Data

US 2022/0389479 A1 Dec. 8, 2022

Related U.S. Application Data

(60) Provisional application No. 62/914,318, filed on Oct. 11, 2019.

(51) Int. Cl.
*C12Q 1/56* (2006.01)
*C12Q 1/37* (2006.01)

(52) U.S. Cl.
CPC ................. *C12Q 1/56* (2013.01); *C12Q 1/37* (2013.01); *G01N 2333/96452* (2013.01); *G01N 2400/40* (2013.01)

(58) Field of Classification Search
CPC .. C12Q 1/56; C12Q 1/37; G01N 2333/96452; G01N 2400/40; C07K 16/00
See application file for complete search history.

(56) References Cited

U.S. PATENT DOCUMENTS 5,262,325 A * 11/1993 Zimmermann ........ A61K 38/51 435/200
8,796,430 B2 * 8/2014 Bruckschwaiger .. C07K 16/065 530/424
8,940,877 B2 1/2015 Bruckschwaiger et al.
2007/0037236 A1 * 2/2007 Klein ...................... C12Q 1/56 435/13
2023/0142480 A1 * 5/2023 Mais-Paul ............. C07K 16/18 530/390.1

FOREIGN PATENT DOCUMENTS

JP 2008-195564 A 8/2008
JP 2013-527201 A 6/2013
WO WO 2011-149472 A1 12/2011

OTHER PUBLICATIONS

Manco-Johnson, M.J., et al. 2000. "Heparin neutralization is essential for accurate measurement of factor VIII activity and inhibitor assays in blood samples drawn from implanted venous access devices". Journal of Laboratory and Clinical Medicine, 136(1), pp. 74-79. (Year: 2000).*
Gervin. "The Heparin Unit: A Source of Medical Misunderstanding." Arch Surg. 1975; 110(6): 761. doi: 10.1001/archsurg.1975.01360120079019 (Year: 1975).*
Heparin Sodium; Drugs.com; < www.drugs.com/monograph/heparin-sodium.html>; 15 pages total. (Year: 2024).*
McNeely, T.B. and Griffith, M.J., 1985. The Anticoagulant Mechanism of Action of Heparin in Contact-Activated Plasma: Inhibition of Factor X Activation. Blood, 65(5), pp. 1226-1231 (Year: 1985).*
Wolberg et al., 2000. "Coagulation Factor XI is a Contaminant in Intravenous Immunoglobulin Preparations". American Journal of Hematology 65:30-34 (Year: 2000).*
Hooper et al. "Intravenous immunoglobulins: evolution of commercial IVIG preparations." Immunol Allergy Clin North Am. Nov. 2008;28(4):765-78 (Year: 2008).*
"Frontiers vol. 74 Devotion to hematologic study", [online], Jan. 13, 2017, Funakoshi Co., Ltd. HP, [Searched: Jun. 12, 2024], Internet <URL:https://www.funakoshi.co.jp/contents/66058>.
Alving, B M et al. "Contact-activated factors: contaminants of immunoglobulins preparations with coagulant and vasoactive properties." The Journal of laboratory and clinical medicine vol. 96,2 (1980): 334-46.
Cumming, A M et al. "In vitro neutralization of heparin in plasma prior to the activated partial thromboplastin time test: an assessment of four heparin antagonists and two anion exchange resins." Thrombosis research vol. 41,1 (1986): 43-56. doi:10.1016/0049-3848(86)90278-1.
Etscheid, M et al. "Identification of kallikrein and FXIa as impurities in therapeutic immunoglobulins: implications for the safety and control of intravenous blood products." Vox sanguinis vol. 102,1 (2012): 40-6. doi:10.1111/j.1423-0410.2011.01502.x.
Hutt, E D, and H S Kingdon. "Use of heparinase to eliminate heparin inhibition in routine coagulation assays." The Journal of laboratory and clinical medicine vol. 79,6 (1972): 1027-34.
International Preliminary Report on Patentability for International Patent Application No. PCT/US2020/54881 dated Apr. 12, 2022, 6 pages.

(Continued)

*Primary Examiner* — Anand U Desai
*Assistant Examiner* — Andrew T Moehlman
(74) *Attorney, Agent, or Firm* — Morgan, Lewis & Bockius LLP

(57) ABSTRACT

The present invention provides a heparin-insensitive assay for measuring the quantity of Factor XIa in a sample. The present invention provides a method for measuring the concentration of Factor XIa in a plasma sample by using enzymatic heparin degradation as sample pretreatment step.

22 Claims, 4 Drawing Sheets

(56) References Cited

OTHER PUBLICATIONS

International Search Report and Written Opinion for International Patent Application No. PCT/US2020/54881 dated Dec. 1, 2020, 7 pages.
Lebing, W et al. "Properties of a new intravenous immunoglobulin (IGIV-C, 10%) produced by virus inactivation with caprylate and col. chromatography." Vox sanguinis vol. 84,3 (2003): 193-201. doi:10.1046/j.1423-0410.2003.00285.x.
Manco-Johnson, M J et al. "Heparin neutralization is essential for accurate measurement of factor VIII activity and inhibitor assays in blood samples drawn from implanted venous access devices." The Journal of laboratory and clinical medicine vol. 136,1 (2000): 74-79. doi:10.1067/mlc.2000.107299.
Park, Dong Hwarn et al. "A new manufacturing process to remove thrombogenic factors (II, VII, IX, X, and XI) from intravenous immunoglobulin gamma preparations." Biologicals : journal of the International Association of Biological Standardization vol. 45 (2017): 1-8. doi:10.1016/j.biologicals.2016.11.002.
Puy, Cristina et al. "Endothelial PAI-1 (Plasminogen Activator Inhibitor-1) Blocks the Intrinsic Pathway of Coagulation, Inducing the Clearance and Degradation of FXIa (Activated Factor XI)." Arteriosclerosis, thrombosis, and vascular biology vol. 39,7 (2019): 1390-1401. doi:10.1161/ATVBAHA.119.312619.
Seifner, Alexandra et al. "Assessment of immunoglobulin concentrates on thrombogenic activity by thrombin generation assay, prekallikrein activator assay, and size-exclusion chromatography." Transfusion vol. 54,2 (2014): 376-83. doi:10.1111/trf.12280.
Tanaka et al., *Braz J Med Biol Res* 2000 (33)37-30.
Teschner, W et al. "A new liquid, intravenous immunoglobulin product (IGIV 10%) highly purified by a state-of-the-art process." Vox sanguinis vol. 92,1 (2007): 42-55. doi:10.1111/j.1423-0410.2006.00846.x.
Wolberg, A S et al. "Coagulation factor XI is a contaminant in intravenous immunoglobulin preparations." American journal of hematology vol. 65,1 (2000): 30-4. doi:10.1002/1096-8652(200009)65:1<30::aid-ajh5>3.0.co;2-j.
Yamashita, A. et al. "Neutralization effect of heparinase by thrombin generation test for the assessment of blood samples containing heparin." Japanese Journal of Thrombosis and Hemostasis, 2008, vol. 19, Issue 6, pp. 796-805, https://doi.org/10.2491/jsth.19.796.
Yang, V C et al. "Heparinase immobilization. Characterization and optimization." Annals of the New York Academy of Sciences vol. 542 (1988): 515-520. doi:10.1111/j.1749-6632.1988.tb25880.x.

* cited by examiner

HEPARIN-INSENSITIVE ASSAY FOR FACTOR XIA

BACKGROUND OF THE INVENTION

Plasma-derived blood products are used to treat not only a variety of blood disorders, but diseases of other origin. For example, immune globulin (IgG) products from human plasma were first used in 1952 to treat immune deficiency. Since then, IgG preparations have found widespread use in at least three main categories of medical conditions: (1) immune deficiencies such as X-linked agammaglobulinemia, hypogammaglobulinemia (primary immune deficiencies), and acquired compromised immunity conditions (secondary immune deficiencies), featuring low antibody levels; (2) inflammatory and autoimmune diseases; and (3) acute infections.

Plasma-derived therapeutic proteins, unlike other biologics that are produced via recombinant expression of DNA vectors in host cell lines, are fractionated from human blood and plasma donations. A number of IVIG preparation methods are used by commercial suppliers of IVIG products. One common problem with the current IVIG production methods is the substantial loss of IgG during the purification process, estimated to be at least 30% to 35% of the total IgG content of the starting material. One challenge is to maintain the quality of viral inactivation and lack of impurities which can cause adverse reactions, while bolstering the yield of IgG. Studies have suggested that administration of high levels of amidolytic activity may result in unwanted thromboembolic events (Wolberg A S et al., Coagulation factor XI is a contaminant in intravenous immunoglobulin preparations. *Am J Hematol* 2000; 65:30-34; Alving B M et al., Contact-activated factors: contaminants of immunoglobulin preparations with coagulant and vasoactive properties. *J Lab Clin Med* 1980; 96:334-346; Seifner A, et al (2013): *Transfusion* 2013, Assessment of immunoglobulin concentrates on thrombogenic activity by thrombin generation assay, prekallikrein activator assay, and size-exclusion chromatography, dx.doi.org/10.1111/trf.12280; and Etscheid M, et al (2012): *Vox Sanguinis* 102(1), 40-6, Identification of kallikrein and FXIa as impurities in therapeutic immunoglobulins: implications for the safety and control of intravenous blood products).

At the current production levels of IVIG, what may be considered small increases in the yield are in fact highly significant. For example at 2007 production levels, a 2% increase in efficiency, equal to an additional 56 milligrams per liter, would generate 1.5 additional metric tons of IVIG.

Various modern methods employ a precipitation step, such as caprylate precipitation (Lebing et al., *Vox Sang* 2003 (84):193-201) and Cohn Fraction (I+)II+III ethanol precipitation (Tanaka et al., *Braz J Med Biol Res* 2000 (33)37-30) coupled to column chromatography. Most recently, Teschner et al. (*Vox Sang,* 2007 (92):42-55) have described a method for production of a 10% IVIG product in which cryo-precipitate is first removed from pooled plasma and then a modified Cohn-Oncley cold ethanol fractionation is performed, followed by S/D treatment of the intermediate, ion exchange chromatography, nanofiltration, and optionally ultrafiltration/diafiltration. However, despite the improved purity, safety, and yield afforded by these IgG manufacturing methods, a significant amount of IgG is still lost during the purification process. The starting material for the ethanol fractionation process can have underwent different adsorption steps to obtain intermediates for the purification of coagulation factors and plasma protein inhibitors. C1-inhibitor is the most important physiological inhibitor of plasma kallikrein, Factor XIa and Factor XIIa and depletion of C1-inhibitor can result in accumulation of these factors in upstream starting materials of commercial IgG therapeutics such as GAMMAGARD® LIQUID.

Factor XIa is a plasma serine protease involved in the regulation of blood coagulation. While blood coagulation is a necessary and important part of the regulation of an organism's homeostasis, abnormal blood coagulation can also have deleterious effects. The potent anticoagulant activity of heparin can be utilized during plasma fractionation processes to prevent unwished activation of coagulation factors plasma kallikrein, Factor XIa, factor XIIa etc. Several studies have suggested that administration of high levels of amidolytic activity may result in unwanted thromboembolic events (Wolberg A S et al., Coagulation factor XI is a contaminant in intravenous immunoglobulin preparations. Am J Hematol 2000; 65:30-34; and Alving B M et al., Contact-activated factors: contaminants of immunoglobulin preparations with coagulant and vasoactive properties. J Lab Clin Med 1980; 96:334-346).

Thus, to ensure the adequate removal of thrombosis generating agents (TgAs) from the plasma sample during the IgG preparation, heparin is added to increase the TgA removal potency of the manufacturing process. However, residual heparin can interfere with the FXIa activity assay even at low concentrations.

Several approaches have been attempted to circumvent the heparin interference problem prior to the assay. Ion exchange resins have been used to adsorb heparin from the sample prior to testing, as described by Cumming, et al., *Thrombosis Res.* 41:43-56 (1986). This method is non-specific, removing coagulation factors and other blood proteins in addition to heparin, thereby influencing the test result.

Protamine sulfate has been used to neutralize heparin by electrostatic interaction and precipitation, as also reported by Cumming, et al., (1986). However, protamine sulfate itself interferes with the chromogenic FXIa assay and is not able to neutralize the anticoagulant effect of low molecular weight heparins.

Hutt and Kingdon, *J. Lab. Clin. Med.* 79:1027 (1972), attempted to use a heparinase from *Flavobacterium heparinum* to treat plasma samples prior to performing PTT analysis. However, their data indicated their inability to completely remove the interfering moiety.

The most desirable resolution to the heparin interference problem would be a method that could expeditiously and specifically remove heparin from plasma samples immediately before the onset of the assay for Factor XIa, without interfering the assay. The anticoagulant, inhibitory activity of heparin should be neutralized, making the sample essentially free of heparin, while the reagent, itself, should not impart any effects on plasma sample.

Due to rising concerns over the presence of serine protease and serine protease zymogens in a plasma sample or a plasma-derived protein preparations, there exists an immediate need in the art for a heparin-insensitive assay for these serine protease, particularly factor FXIa.

SUMMARY OF THE INVENTION

It has now been found that a general method for removing interference from heparin (e.g., inhibition) in protein assays includes the step of degrading the heparin in the sample, for example, by enzymatic degradation, e.g., treating the sample with heparinase prior to performing the assay. The method is robust and specific for heparin, leaving non-heparin proteins in the sample substantially non-degraded and readily assayable. Among other aspects, the present invention provides a heparin-insensitive assay for determination of the quantity of a protein in a sample in which the presence of heparin interferes with determining the quantity of the protein. Exemplary protein assays include those for serine protease and serine protease zymogens. Exemplary samples include a plasma sample, e.g., a plasma fraction, and plasma-derived protein preparations. Other samples include, without limitation, a cell culture supernatant. In an exemplary embodiment the assay determines the quantity of a serine protease and/or a serine protease zymogen in a plasma sample, or plasma-derived protein preparations. In various embodiments, the present invention provides a method for measuring the Factor XIa activity in a plasma sample.

The method provided herein for the determination of protein quantity, e.g., the measurement of FXIa, shows complete removal of inhibitory effect of heparin on the assay, resulting in 100% recovery of FXIa. In a particularly important aspect, the present invention provides methods that significantly increase the efficiency of a protein assay, as compared to state of the art methods used for assaying a protein, e.g., FXIa, in a sample. In one embodiment, in which FIXa is the protein quantified, these improved results are achieved by adding heparinase I to the plasma sample containing heparin and incubating the resulting mixture at +37° C. for 5 min before running the protein, e.g., FXIa assay. The inhibitory effect of heparin on the assay is fully reversed by pre-incubating the heparin-containing plasma samples with heparinase I. Though exemplified by reference to an assay for FIXa in a plasma sample, the invention is of sufficient breadth to be of general use in samples (e.g., protein samples) containing heparin in which heparin interferes with the assay unless it is inactivated or removed.

In one aspect, the present invention provides a method of detecting and/or quantifying Factor XIa (FXIa) in a sample containing heparin, comprising:

a) incubating the sample containing heparin with heparinase, essentially eliminating any heparin-dependent inhibition therein, thereby producing a heparin-depleted sample; and b) detecting and/or quantitating FXIa in the sample by measuring activity of activated proteins in the heparin-depleted sample. An exemplary sample is a plasma sample of a plasma-derived protein preparation.

In another aspect, the present invention provides a method of detecting and/or quantifying Factor XIa (FXIa) in a plasma sample containing heparin, comprising:

a) incubating the plasma sample containing heparin with heparinase, essentially eliminating any heparin-dependent inhibition therein, thereby producing a heparin-depleted sample; and b) detecting and/or quantitating FXIa in the sample by measuring activity of activated proteins in the heparin-depleted sample.

In another aspect, the present invention provides a method of detecting and/or quantifying Factor XIa (FXIa) in a plasma sample containing heparin, comprising: a) incubating the plasma sample containing heparin with heparinase, essentially eliminating any heparin-dependent inhibition therein, thereby producing a heparin-depleted sample; b) adding a defined amount of FIX to the heparin-depleted sample and incubating the sample, thereby converting Factor IX to Factor IXa; c) adding a defined amount of FX to the sample and incubating the sample, thereby activating factor Xa in the sample; and d) detecting and/or quantitating FXIa in the sample by measuring activity of Factor Xa in the sample.

In one embodiment of the methods described above, the heparinase comprises a member selected from heparinase I, heparinase II, heparinase III and a mixture thereof.

In one embodiment of the methods described above, the sample comprises blood, plasma and mixtures containing purified proteins from natural, synthetic or recombinant origin.

In one embodiment of the methods described above, the plasma sample comprises IgG. In various embodiments, the IgG is derived from plasma or plasma fractions.

In one embodiment of the methods described above, the plasma sample comprises IgG derived from cryo-poor plasma.

In one embodiment of the methods described above, the plasma sample comprises IgG derived from a C1-esterase inhibitor depleted cryo-poor plasma.

In one embodiment of the methods described above, the plasma sample comprises IgG derived from a plasma supernatant after C1-esterase inhibitor adsorption of cryo-poor plasma.

In one embodiment of the methods described above, the plasma sample comprises IgG derived from a double-depleted cryo-poor plasma (DDCPP).

In one embodiment of the methods described above, the method further comprises running an in vitro or in vivo activity assay.

In one embodiment of the methods described above, the method further comprises running an in vitro chromogenic assay.

In one embodiment of the methods described above, heparin is present in the sample at a concentration of at least 0.1 IU heparin/mL of sample.

In one embodiment of the methods described above, the heparin is present in the sample at a concentration of from about 0.1 IU heparin/mL of sample to about 50 IU heparin/mL of sample.

In one embodiment of the methods described above, the heparin is present in the sample at a concentration of from about 0.1 IU heparin/mL of sample to about 4 IU heparin/mL of sample.

In one embodiment of the methods described above, the heparin is present in the sample at a concentration of from about 0.1 IU heparin/mL of sample to about 3 IU heparin/mL of sample.

In one embodiment of the methods described above, the heparin is present in the sample at a concentration of about 0.5 IU heparin/mL of sample.

In one embodiment of the methods described above, the heparin is present in the sample at a concentration of about 1 IU heparin/mL of sample.

In one embodiment of the methods described above, the heparinase is present in the sample at a concentration of at least 0.1 U heparinase/mL of sample.

In one embodiment of the methods described above, the heparinase is present in the sample at a concentration from about 0.1 U heparinase/mL of sample to about 10 U heparinase/mL of sample.

In one embodiment of the methods described above, the heparinase is present in the sample at a concentration of about 0.2 U heparinase/mL.

In one embodiment of the methods described above, the heparinase is present in the sample at a concentration of about 5 U heparinase/mL.

In one embodiment of the methods described above, the heparinase is present in the sample of a) at concentration of about 10 U heparinase/mL.

In one embodiment of the methods described above, the heparin and heparinase is in a ratio of at least about 1:0.01.

In one embodiment of the methods described above, the heparin and heparinase is in a ratio from about 1:0.01 to about 1:1.

In one embodiment of the methods described above, the sample is incubated with the heparinase for from about 1 to about 7200 seconds.

In one embodiment of the methods described above, the sample is incubated with the heparinase for from about 10 to about 7200 seconds.

In one embodiment of the methods described above, the sample is incubated with the heparinase for about 300 seconds.

In one embodiment of the methods described above, the sample is incubated with the heparinase for about 7200 seconds.

In one embodiment of the methods described above, the sample is incubated at a temperature from about 20° C. to about 40° C.

In one embodiment of the methods described above, the sample is incubated at a temperature from about 20° C. to about 30° C.

In one embodiment of the methods described above, the sample is incubated at a temperature of about 37° C.

In one embodiment of the methods described above, the heparin-depleted sample is essentially free of heparin.

In one embodiment of the methods described above, the heparin-depleted sample is completely free of heparin.

In another aspect, the present invention provides a kit for carrying out the methods of detecting and/or quantifying Factor XIa (FXIa) in a plasma sample containing heparin, comprising: a) a first vial containing heparinase; b) a second vial containing one or more reagents to detect the presence of FXIa; and c) instructions directing a user of the kit in its use.

DETAILED DESCRIPTION OF THE INVENTION

A. Introduction

C1-inhibitor (C1-inh, C1 esterase inhibitor) is the most important physiological inhibitor of plasma kallikrein, Factor XIa and Factor XIIa and depletion of C1-inhibitor can result in accumulation of these factors in starting materials for the manufacture of commercial IgG therapeutics such as GAMMAGARD® LIQUID (GGL), making it challenging to produce IgG preparation for intravenous administration without elevated risk of thromboembolic events. Due to the complexity of the production of immunoglobulins out of the plasma supernatants after adsorption of C1-inhibitor, termed as double depleted cryo-poor plasma (DDCPP), the native supernatant is not used as a starting material for the manufacture of IgG. Thus, to ensure the adequate removal of plasma kallikrein, Factor XIa and Factor XIIa with clearly reduced concentration of the C1-inhibitor, a calculated amount of 10,000 IU/L heparin is added to DDCPP before the alcohol fractionation process is initiated. The final products obtained were shown to contain residual heparin concentrations of less than 1 IU/mL, corresponding to the quantification limit of the chromogenic heparin assay however, heparin interferes with the FXIa activity assays even at the lowest concentration of 0.1 U/mL.

The present disclosure is based in part on the discovery that heparin is used as an anticoagulant during the plasma fractionation process however, heparin interferes with FXIa activity assays even at the lowest concentration of 0.1 U/mL, where only 59.2% of the nominal FXIa concentration could be recovered, resulting in 48.8% assay inhibition. At a heparin concentration of 1 IU/mL, representing the limit of quantification for the FXIa assays in GGL, the recovery of FXIa was only 7.1%, corresponding to an assay inhibition of 92.8%. In some embodiments, the FXIa activity assays include assays to determine procoagulant activity, amidolytic activity or Factor XI zymogen. In some embodiments, the FXIa activity assays include thrombin generation assay (TGA), non-activated partial thromboplastin time (NAPTT) assay, FXIa determination with a Factor IX (FIX) based assay, in vivo wessler test, FXIa chromogenic assay, ELISA assay.

The present disclosure is based in part on the discovery that heparin is used as anticoagulant during the plasma fractionation process however, heparin interferes with the FXIa chromogenic assays even at the lowest concentration of 0.1 U/mL, where only 59.2% of the nominal FXIa concentration could be recovered, resulting in 48.8% assay inhibition. At a heparin concentration of 1 IU/mL, representing the limit of quantification for the FXIa chromogenic assays in GGL, the recovery of FXIa was only 7.1%, corresponding to an assay inhibition of 92.8%.

Figure 3:
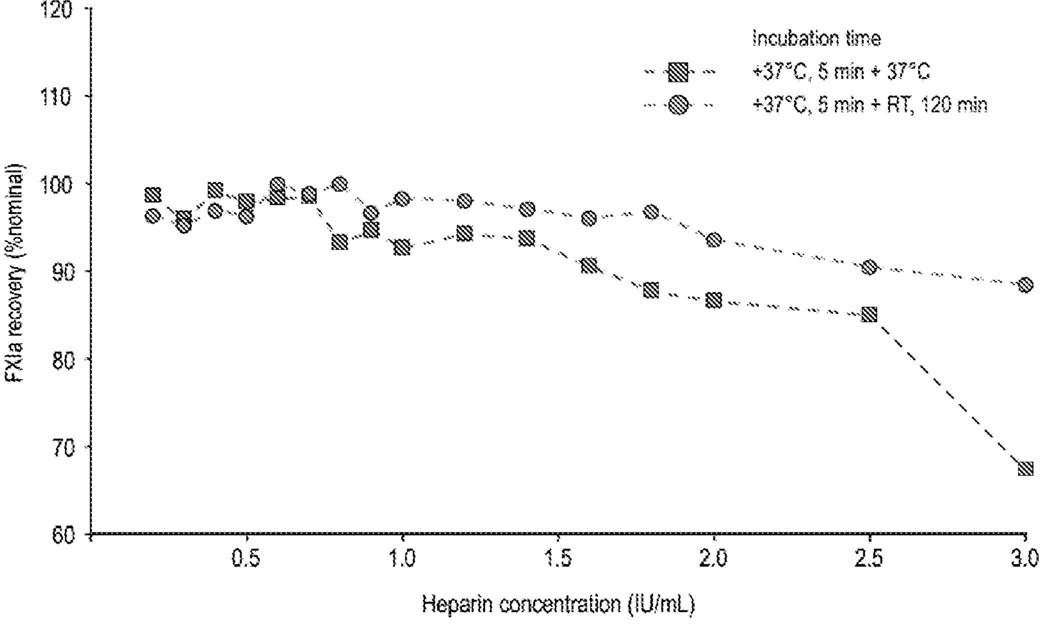
FIG. 3 shows heparin concentration study in assay buffer.

Using enzymatic heparin degradation as a sample pretreatment step, allows further use of the FXIa chromogenic assay. The present disclosure is thus also based in part on the discovery of the enzymatic breakdown of heparin with heparinase to effectively remove the pronounced inhibitory effect of heparin on the FXIa chromogenic assay. For example, FIG. 3 summarizes the results of an experiment in which heparin was added to a FXIa reference standard (7.8 mIU/mL) followed by heparinase (from *Flavobacterium heparinum*, Sigma, H2519) effecting heparin digestion before executing the ROX FXIa Chromogenic Assay. In the experiment, 0.2 IU/mL heparin was added to the sample, resulting in 55% recovery of the FXIa nominal concentration (an inhibitory result on the assay). On the other hand, heparinase I, added to the FXIa sample at a concentration of 0.2 U/mL and incubated at +37° C. for 5 min before running the ROX FXIa Chromogenic Assay, resulted in 101% recovery of the FXIa nominal concentration. This shows that the inhibitory effect of heparin on the ROX FXIa Chromogenic Assay could be fully reversed by pre-incubating the heparin-containing FXIa samples with heparinase I.

In an exemplary embodiment, the present invention thus provides a method of detecting and/or quantifying Factor XIa contained in a plasma sample. In one embodiment of the method, the plasma sample containing heparin is incubated with heparinase to eliminate any heparin dependent inhibition therein. Factor IX is then added to said sample and FXIa activates human FIX to FIXa in the presence of calcium ions. Generated FIXa then activates human Factor FX to activated Factor X, (hereafter referred to as Factor Xa). The amount of Factor Xa produced in this reaction is directly proportional to the activity of Factor XIa in the sample. An indicator agent is added to the reaction mixture, which reacts with the Factor Xa so formed, to release a signal molecule, which is then conveniently measured.

In accordance with the method of this invention, a heparin-insensitive assay is provided which has a higher degree of recovery of Factor XIa. Another object of this invention is to provide a kit for the convenient performance of assays of Factor XIa-containing plasma sample.

As will be apparent to those of skill in the art, the discovery underlying the instant invention is of broad generality, applicable to a protein sample containing heparin in which the heparin would interfere with a desired process, e.g. and assay to characterize and/or quantify the protein in the protein sample. Further exemplary advantages, objects and aspects of the present invention are set for the hereinbelow.

B. Definitions

As used herein, the term "Intravenous IgG" or "IVIG" treatment refers generally to a therapeutic method of intravenously, subcutaneously, or intramuscularly administering a composition of IgG immunoglobulins to a patient for treating a number of conditions such as immune deficiencies, inflammatory diseases, and autoimmune diseases. The IgG immunoglobulins are typically pooled and prepared from plasma. Whole antibodies or fragments can be used. IgG immunoglobulins can be formulated in higher concentrations (e.g., greater than 10%) for subcutaneous administration, or formulated for intramuscular administration. This is particularly common for specialty IgG preparations which are prepared with higher than average titers for specific antigens (e.g., Rho D factor, pertussis toxin, tetanus toxin, botulism toxin, rabies, etc.). For ease of discussion, such subcutaneously or intramuscularly formulated IgG compositions are also included in the term "IVIG" in this application.

As used herein, the term "amidolytic activity" refers to the ability of a polypeptide to catalyze the hydrolysis of at least one peptide bond in another polypeptide. The amidolytic activity profile for an IgG immunoglobulin composition may be determined by assaying with various chromogenic substrates, with different specificities for proteases found in human plasma, including without limitation: PL-1 (broad spectrum), S-2288 (broad spectrum), S-2266 (FXIa, glandular kallikreins), S-2222 (FXa, trypsin), S-2251 (Plasmin), and S-2302 (Kallikrein, FXIa, and FXIIa). Methods for determining the amidolytic activity of a composition are well known in the art, for example, as described in M. Etscheid et al. (Identification of kallikrein and FXIa as impurities in therapeutic immunoglobulins: implications for the safety and control of intravenous blood products, Vox Sang 2011; the disclosure of which is hereby expressly incorporated by reference in its entirety for all purposes.)

As used herein, the term "C1-inhibitor (C1-inh, C1 esterase inhibitor)" is a protease inhibitor belonging to the serpin superfamily. Its main function is the inhibition of the complement system to prevent spontaneous activation. C1-inhibitor is an acute-phase protein that circulates in blood at levels of around 0.25 g/L. The levels rise ~2-fold during inflammation. C1-inhibitor irreversibly binds to and inactivates C1r and C1s proteases in the C1 complex of classical pathway of complement. MASP-1 and MASP-2 proteases in Mannose-binding lectin (MBL) complexes of the lectin pathway are also inactivated. This way, C1-inhibitor prevents the proteolytic cleavage of later complement components C4 and C2 by C1 and MBL. Although named after its complement inhibitory activity, C1-inhibitor also inhibits proteases of the fibrinolytic, clotting, and kinin pathways. Note that C1-inhibitor is the most important physiological inhibitor of plasma kallikrein, FXIa, and FXIIa.

As used herein, "cryo-poor plasma" refers to the supernatant formed after the cold precipitation (cryo-precipitation) of plasma or pooled plasma at temperatures nearing freezing, e.g., at temperatures below about 10° C. In the context of the present invention, plasma may refer interchangeably to recovered plasma (i.e., plasma that has been separated from whole blood ex vivo) or source plasma (i.e., plasma collected via plasmapheresis). Cryo-precipitation is commonly performed, for example, by thawing previously frozen pooled plasma, which has already been assayed for safety and quality considerations, although fresh plasma may also be used. Thawing is typically carried out at a temperature no higher than 6° C. After complete thawing of the frozen plasma at low temperature, centrifugation is performed in the cold (e.g., ≤6° C.) to separate solid cryo-precipitates from the liquid supernatant. Alternatively, the separation step can be performed by filtration rather than centrifugation.

As used herein, the term "sample" refers to a biological (e.g., blood, plasma and mixtures containing purified proteins from natural, synthetic or recombinant origin) and non-biological origin. An exemplary sample contains at least one protein As used herein, "protein sample' refers to a sample containing at least one protein of interest. The sample is interrogated using an assay and the assay is one in which the presence of heparin will interfere with the results desired from the interrogation. The protein sample is such that its treatment with heparinase in an amount effective to eliminate heparin interference in the assay does not interfere with the interrogation of the sample or its results.

As used herein, the term "plasma sample" refers to any suitable material, for example, recovered plasma or source plasma or plasma fractions or plasma supernatants or plasma derived protein preparations. An exemplary "plasma sample" includes an IgG derived from plasma or plasma fractions, an IgG derived from cryo-poor plasma, an IgG derived from a C-1 esterase inhibitor adsorption of cryo-poor plasma, an IgG derived from a double-depleted cryo-poor plasma (DDCPP).

As used herein, the "double depleted cryo-poor plasma (also known as DDCPP/C-1 esterase inhibitor depleted cryo-poor plasma") refers to the adsorption supernatant formed after the adsorption of C1-inhibitor of cryo-poor plasma at temperatures nearing freezing, e.g., at temperatures below about 8° C. GAMMAGARD® LIQUID (Baxter Healthcare Corporation, Westlake Village, CA) manufacturing process employs a modified Cohn-Oncley cold ethanol fractionation procedure to isolate an intermediate immunoglobulin G (IgG) fraction, referred to as Precipitate G (PptG), from frozen human plasma pools. PptG is further purified through the subsequent use of weak cation and weak anion exchange chromatography. Three dedicated virus reduction steps are included in the downstream purification of PptG, which are solvent/detergent treatment, nanofiltration, and incubation at low pH and elevated temperature in the final formulation. The starting material for the ethanol fractionation process can undergo different adsorption steps to obtain intermediates for the purification of coagulation factors and plasma protein inhibitors. The adsorption supernatant obtained after the adsorption of C1-inhibitor in the CINRYZE® manufacturing process is termed as double depleted cryo-poor plasma (DDCPP).

As used herein, "heparin-depleted sample" refer to sample with essentially free from the inhibitory effect of heparin or sample with complete removal of inhibitory effect of heparin.

As used herein, "FXIa activity assay" refer to any in vivo or in vitro assays to determine procoagulant activity, amidolytic activity or Factor XI zymogen. FXIa activity assays include thrombin generation assay (TGA), non-activated partial thromboplastin time (NAPTT) assay, FXIa determination with a Factor IX (FIX) based assay, in vivo wessler test, FXIa chromogenic assay, ELISA assay.

As used herein, "kits" are understood to contain at least the non-standard laboratory reagents for use in the methods of the invention, such as the specific reagents required for the use in the method and the protein at a known amount or concentration to act as a positive control in the method of the invention. The kit can further include any other components required to practice the method of the invention, as dry powders, concentrated solutions, or ready to use solutions. In some embodiments, the kit comprises one or more containers that contain reagents for use in the methods of the invention; such containers can be boxes, ampules, bottles, vials, tubes, bags, pouches, blister-packs, or other suitable container forms known in the art. Such containers can be made of plastic, glass, laminated paper, metal foil, or other materials suitable for holding reagents.

As used herein, "chromogenic assay" refer to any laboratory test that relies on the change in color of a reagent to indicate its presence.

As used herein, "Rossix Assay" or "ROX FXIa Chromogenic Assay" refer to a chromogenic kit for quantitative activity determination of Factor XIa in enriched or highly purified protein preparations.

C. Preparation of Double Depleted Cryo-Poor Plasma

An exemplary sample, e.g., a plasma fraction sample, in which for detecting and/or quantifying Factor XIa (FXIa) is of interest consists of double depleted cryo poor plasma—the adsorption supernatant obtained after the adsorption of C1-inhibitor in the CINRYZE® manufacturing process. The purification process typically starts with thawing previously frozen pooled plasma, which preferably has already been assayed for safety and quality considerations. Thawing is typically carried out at a temperature no higher than 6° C. After complete thawing of the frozen plasma at low temperature, centrifugation is performed in the cold (e.g., ≤6° C.) to separate solid cryo-precipitates from the liquid supernatant. Alternatively, the separation step is performed by filtration rather than centrifugation. The liquid supernatant (also referred to as "cryo-poor plasma," after cold-insoluble proteins are removed by centrifugation from fresh thawed plasma) then undergoes one or more adsorption step to obtain intermediates for the purification of coagulation factors and plasma protein inhibitors. The adsorption supernatant obtained after the adsorption of C1-inhibitor from the cryo-poor plasma is termed as double depleted cryo-poor plasma (DDCPP).

D. Preparation of Plasma Sample with Heparin

Double depleted cryo-poor plasma (DDCPP) is generally not considered an ideal starting material for the manufacture of IgG as depletion of C1-inhibitor can result in accumulation of plasma kallikrein, Factor XIa, and Factor XIIa. To ensure the adequate removal of these factors with clearly reduced concentration of the C1-inhibitor, a calculated amount of 10,000 IU/L heparin is added to DDCPP before the alcohol fractionation process is initiated. The final IgG product obtained is shown to contain residual heparin concentrations of less than 1 IU/mL

Figure 1:
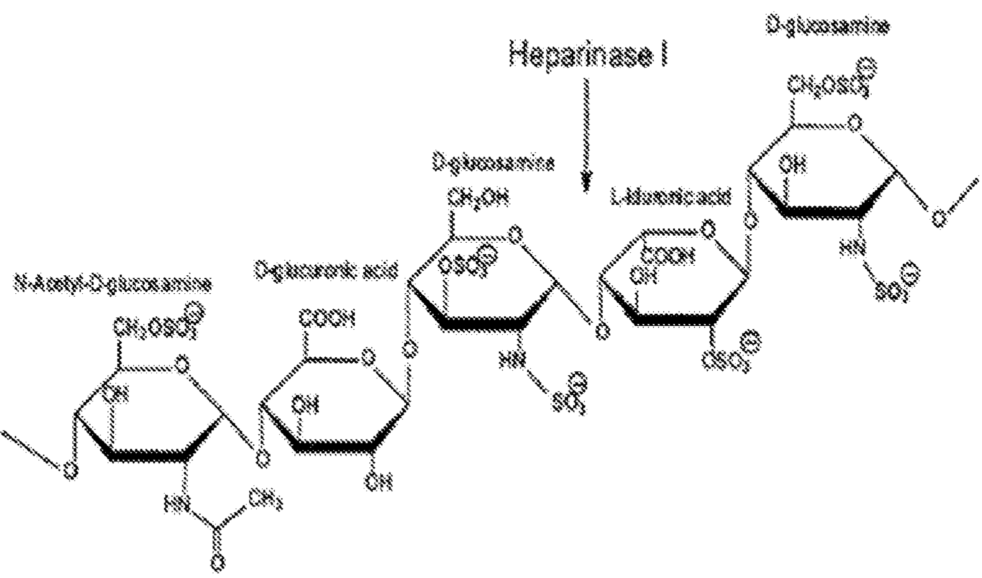
FIG. 1 shows the reaction mechanism of heparinase I.

E. Reversal of Heparin Influence on the ROX FXIa Chromogenic Assay by Heparinase The anticoagulant influence of heparin is removed by enzymatic breakdown of heparin, using heparinase, e.g., heparinase I. Heparinase I cleaves the heparin polysaccharide chains at linkages between hexosamines and O-sulfated iduronic acids, yielding mainly disaccharides containing unsaturated uronic acids. These disaccharides lack anticoagulant activity, but can still bind to coagulation proteins. One Sigma unit heparinase I will form 0.1 μmole of unsaturated uronic acid per hour at pH 7.5 at 25° C. using heparin sodium as substrate, while the International Unit is defined as the amount of heparinase forming 1 μmol of unsaturated uronic acid per minute. One International Unit is equivalent to about 600 Sigma units. FIG. 1 shows the reaction mechanism of heparinase I.

Figure 2:
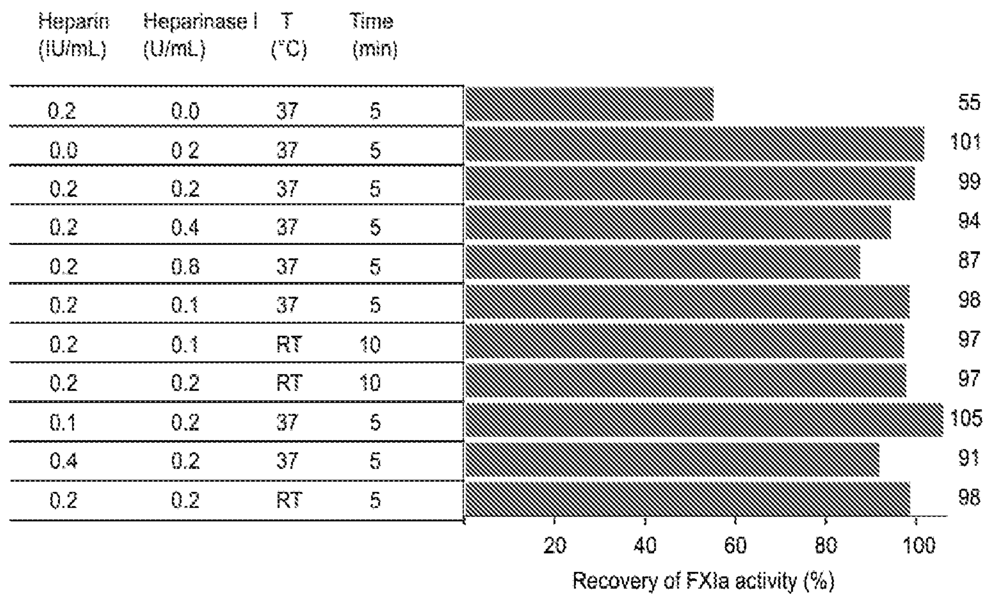
FIG. 2 shows data on reversed inhibitory effect of heparin by heparinase I.

This enzymatic breakdown of heparin to disaccharides, described to fully eliminate its anticoagulant activity, was assessed to provide a potential method for eliminating the inhibitory influence of heparin on the ROX FXIa Chromogenic Assay. FIG. 2 summarizes the results of the first run, where heparin was added to the FXIa reference standard (7.8 mIU/mL) followed by heparinase (from *Flavobacterium heparinum*, Sigma, H2519) digestion before executing the ROX FXIa Chromogenic Assay.

F. Rossix Assay—Rox Factor FXIa (Measurement Principle)

In an exemplary embodiment, FXIa functional activity is determined in a chromogenic method. In an exemplary assay, FXIa in the sample activates human FIX to FIXa in the presence of calcium ions. Generated FIXa activates human FX in the presence of human FVIII, calcium ions and phospholipid. The amount of activated FX is determined from the hydrolysis of a chromogenic FXa substrate and is related to the FXIa activity of the sample. The concentration of functionally active FXIa is assigned vs. a FXIa Calibrator and expressed in Units.

The present invention is further illustrated by the non-limiting examples set forth hereinbelow.

EXAMPLES

The following examples are provided by way of illustration only and not by way of limitation. Those of skill in the art will readily recognize a variety of non-critical parameters that could be changed or modified to yield essentially the same or similar results.

Example 1—Influence of Heparin on the Chromogenic FXIa Assay

For the chromogenic FXIa assay (Rossix), all data were generated by the department Method Development Coagulation (Analytical Development, Product Development & Technical Services), where the chromogenic FXIa assay has been qualified for the intended use.

The chromogenic FXIa assay from Rossix (ROX FXIa Chromogenic Assay) uses purified factor IX and factor X to measure the generation of activated factor Xa with a chromogenic substrate selective for FXa dependent on the concentration of FXIa in the test sample. All proteins involved in this reaction sequence are known to contain binding sites for heparin. Unfractionated heparin (lots A [1,041 IU/mL] and B [1,046 IU/mL]) and protamine sulfate (1 mg/mL) were added in different concentrations and as combination in the ratio of 10 μg protamine sulfate per IU heparin to the FXIa standard of the ROX FXIa Chromogenic Assay kit. In a second approach, similar experiments were performed in GAMMAGARD Liquid (GGL), spiked with the FXIa standard. The FXIa assay was carried out according to the standard protocol. Table 1 shows the results obtained for heparin concentrations ranging from 0 to 4 IU/mL added to the FXIa standard. FXIa concentrations are shown in mIU/mL and as percentage of the concentration determined for the sample without heparin (column "Recovery (%)").

TABLE 1

Influence of heparin on the ROX FXIa Chromogenic Assay

| Heparin (IU/mL) | FXIa (mIU/mL) | Recovery (%) |
|---|---|---|
| 0 | 9.17 | 100.0 |
| 0.1 | 5.43 | 59.2 |
| 0.2 | 3.73 | 40.7 |
| 1.0 | 0.65 | 7.1 |
| 2.0 | <0.31 | <3.4 |
| 4.0 | <0.31 | <3.4 |

Unfractionated heparin demonstrated a clear inhibitory influence on the ROX FXIa Chromogenic Assay even at the lowest concentration of 0.1 IU/mL, where only 59.2% of the nominal FXIa concentration could be recovered (48.8% assay inhibition). At a heparin concentration of 1 IU/mL, representing the limit of quantification for the chromogenic heparin assay in GAMMAGARD LIQUID® manufacturing process, the recovery was 7.1%, corresponding to an assay inhibition of 92.8%.

Example 2—Influence of Heparin and Protamine Sulfate on the Chromogenic FXIa Assay Table 2 shows the results (FXIa concentrations and percentage recovery of the nominal FXIa concentration) for FXIa reference standard, where heparin was neutralized with protamine sulfate, using 10 μg protamine sulfate per 1 IU heparin.

TABLE 2

Influence of heparin on the ROX FXIa Chromogenic Assay after neutralization with protamine sulfate

| Heparin (IU/mL) | Protamine sulfate (μg/mL) | FXIa (mIU/mL) | Recovery (%) |
|---|---|---|---|
| 0 | 0 | 9.17 | 100.0 |
| 0.1 | 1 | 8.25 | 89.9 |
| 0.2 | 2 | 8.00 | 87.2 |
| 1.0 | 10 | 6.99 | 76.2 |
| 2.0 | 20 | 6.35 | 69.2 |
| 4.0 | 40 | 3.89 | 42.4 |

The inhibitory effect of heparin on the ROX FXIa Chromogenic Assay is reduced by protamine sulfate, but it did not fully abolish this effect. FXIa ranging from 89.9% to 42.4% was recovered. Recovery decreases with the addition of protamine sulfate concentration, suggesting that there might be an additional inhibitory influence of protamine sulfate on the assay.

Example 3—Influence of Protamine Sulfate on the Chromogenic ROX FXIa Chromogenic Assay Table 3 shows the results, where protamine sulfate was added in increasing concentrations to the FXIa preparation.

TABLE 3

Influence of protamine sulfate on the ROX FXIa Chromogenic Assay

| Protamine sulfate (μg/mL) | FXIa (mIU/mL) | Recovery (%) |
|---|---|---|
| 0 | 9.17 | 100.0 |
| 1 | 9.07 | 98.9 |
| 2 | 8.96 | 97.7 |
| 10 | 7.28 | 79.4 |
| 20 | 5.72 | 62.4 |
| 40 | 3.52 | 38.4 |

Protamine sulfate showed a dose-dependent inhibitory effect on the ROX FXIa Chromogenic Assay although not as pronounced as heparin. Thus, at a concentration of 10 μg/mL (sufficient to neutralize 1 IU heparin/mL) only 79.4% of the nominal FXIa concentration was recovered. These data did not support the implementation of heparin neutralization by protamine sulfate as excess protamine sulfate would interfere with the assay.

Example 4—Influence of Heparin on the Chromogenic ROX FXIa Chromogenic Assay with or without Neutralization with Protamine Sulfate The test series was completed by adding heparin (0.1 to 4 IU/mL) to GGL spiked with the FXIa standard and measuring these samples with (10 μg per IU heparin) and without protamine sulfate neutralization of heparin. Table 4 shows the data obtained, FXIa concentrations in mIU/mL and the percentage recovery of the nominal FXIa concentration.

TABLE 4

Influence of heparin on the ROX FXIa Chromogenic Assay in GGL (spiked with FXIa) with and without neutralization by protamine sulfate

| | Without protamine sulfate | | With protamine sulfate | |
|---|---|---|---|---|
| Heparin (IU/mL) | FXIa (mIU/mL) | Recovery (%) | FXIa (mIU/mL) | Recovery (%) |
| 0 | 12.18 | 100.0 | 12.18 | 100.0 |
| 0.1 | 7.67 | 63.0 | 10.33 | 84.8 |
| 0.2 | 6.28 | 51.6 | 9.95 | 81.7 |
| 1.0 | 1.43 | 11.7 | 9.54 | 78.3 |
| 2.0 | 0.61 | 5.0 | 8.77 | 72.0 |
| 4.0 | <0.31 | <2.55 | 7.62 | 62.5 |

The inhibitory influence of heparin on the ROX FXIa Chromogenic Assay was also seen in the matrix of GGL, spiked with the FXIa preparation. Thus, at a heparin concentration of 1 IU/mL, representing the qualified lower limit of quantification of the heparin assay in the matrix of GGL, the recovery of FXIa was 11.7% (83.3% inhibition). Heparin neutralization with protamine sulfate shows an increase in the recoveries of spiked FXIa. These recoveries, however, did not exceed 84.8% for the lowest heparin concentration and could therefore not assessed to be acceptable. The data obtained for the ROX FXIa Chromogenic Assay, the preferred assay for the measurement of FXIa in GGL and other IgG products, demonstrated an obvious dose-dependent inhibitory influence of heparin. This inhibitory influence could not be reversed by conventional heparin neutralization using protamine sulfate as protamine sulfate itself interferes with the chromogenic FXIa assay.

Example 5—Reversal of the Inhibitory Effect of Heparin by Heparinase

The anticoagulant influence of heparin is removed by enzymatic breakdown of heparin, using heparinase I. The inhibitory effect of 0.2 IU/mL heparin added resulted in 55% recovery of the FXIa nominal concentration. On the other hand, heparinase I, added to the FXIa sample at a concentration of 0.2 U/mL and incubated at +37° C. for 5 min before running the ROX FXIa Chromogenic Assay, resulted in recovery of 101% FXIa. The inhibitory effect of heparin on the ROX FXIa Chromogenic Assay was fully reversed by pre-incubating the heparin-containing FXIa samples with heparinase I. In the next run, increasing heparin concentrations ranging up to 3 IU/mL were treated with a fixed concentration of 0.2 U heparinase I at +37° C. for 5 min before the ROX FXIa Chromogenic Assay was carried out immediately and after keeping the samples for two hours at Room temperature. Table 5 shows the data obtained, giving the FXIa concentrations measured in mIU/mL and the FXIa recovery, expressed as percentage of the concentration obtained without addition of heparin and without heparinase.

TABLE 5

Results of the heparin concentration study in assay buffer

| | | Immediate Measurement | | Measurement after 2 h | |
|---|---|---|---|---|---|
| Heparinase I (U/mL) | Heparin (IU/mL) | FXIa (mIU/mL) | Recovery (%) | FXIa (mIU/mL) | Recovery (%) |
| 0 | 0 | 7.88 | 100.0 | 7.89 | 100.0 |
| 0.2 | 0 | 7.97 | 101.1 | 7.89 | 99.9 |
| 0 | 0.2 | 2.88 | 36.5 | 2.82 | 35.7 |
| 0.2 | 0.2[a)] | 7.78 | 98.8 | 7.60 | 96.4 |
| 0.2 | 0.3 | 7.57 | 96.1 | 7.52 | 95.3 |
| 0.2 | 0.4 | 7.83 | 99.3 | 7.65 | 97.0 |
| 0.2 | 0.5 | 7.73 | 98.1 | 7.60 | 96.3 |
| 0.2 | 0.6 | 7.76 | 98.5 | 7.89 | 100.0 |
| 0.2 | 0.7 | 7.77 | 98.6 | 7.79 | 98.7 |
| 0.2 | 0.8 | 7.36 | 93.4 | 7.89 | 100.0 |
| 0.2 | 0.9 | 7.47 | 94.8 | 7.63 | 96.7 |
| 0.2 | 1.0 | 7.31 | 92.8 | 7.76 | 98.3 |
| 0.2 | 1.2 | 7.44 | 94.4 | 7.74 | 98.1 |
| 0.2 | 1.4 | 7.40 | 93.9 | 7.67 | 97.1 |
| 0.2 | 1.6 | 7.15 | 90.7 | 7.58 | 96.1 |
| 0.2 | 1.8 | 6.93 | 87.9 | 7.64 | 96.8 |
| 0.2 | 2.0 | 6.84 | 86.8 | 7.39 | 93.6 |
| 0.2 | 2.5 | 6.71 | 85.2 | 7.14 | 90.5 |
| 0.2 | 3.0 | 5.32 | 67.5 | 6.98 | 88.5 |

Remark: The data represent the mean of three replicates. The RSDs were not higher than 1.7%.

The data confirmed the inhibitory influence of heparin on the ROX FXIa Chromogenic Assay and that the pre-incubation of the FXIa samples with heparinase I had no influence on the FXIa concentrations determined. The amount of heparinase I (0.2 U/mL) and heparin up to 1.6 IU/mL resulted in FXIa recoveries of higher than 90%, using pre-incubation at +37° C. for 5 min. The efficacy of heparin degradation by heparinase could be increased by prolongation of the incubation time, in particular at heparin concentrations above 1.5 IU/mL. FIG. 3 summarizes the data of example 6 graphically.

Figure 4:
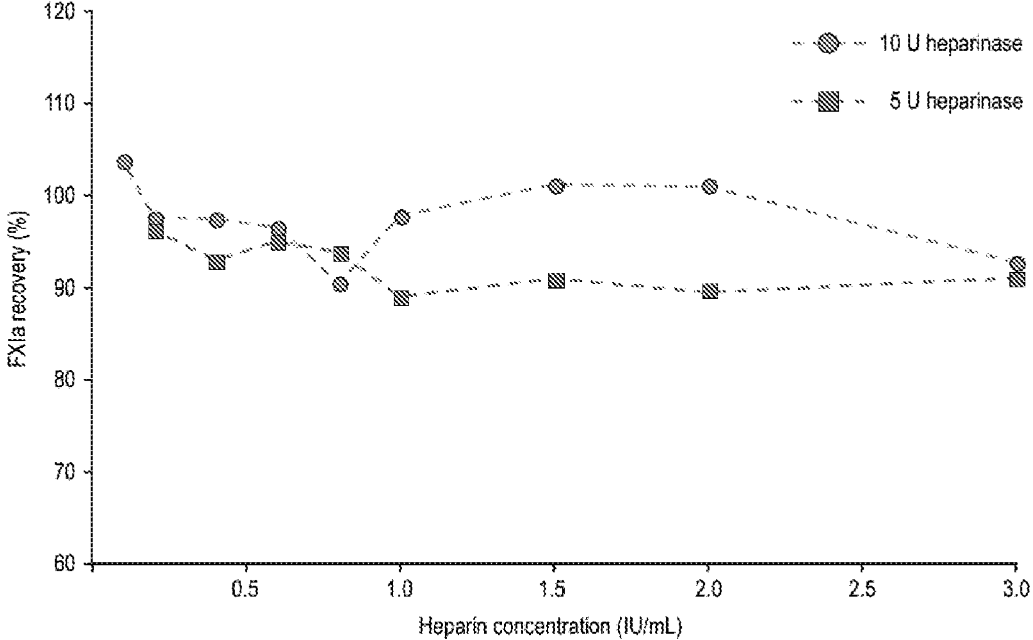
FIG. 4 illustrates heparin concentration study in GAMMAGARD® LIQUID.

Heparin concentrations ranged from 0.1 to 3 IU/mL and the heparinase I concentrations 5 and 10 U/mL were added to the sample. The sample was incubated at Room temperature for 5 min before running the ROX FXIa Chromogenic Assay. Table 6 (also FIG. 4) shows the data obtained. The FXIa-spiked GGL sample had an FXIa concentration of 7.51 mU/mL. The addition of 2 U heparin/mL reduced the FXIa concentration to <0.31 mU/mL (recovery <4.1%).

TABLE 6

Results of the heparin concentration study in GGL spiked with FXIa

| | 10 U heparinase I/mL | | 5 U heparinase I/mL | |
|---|---|---|---|---|
| Heparin (IU/mL) | FXIa (mIU/mL) | Recovery (%) | FXIa (mIU/mL) | Recovery (%) |
| 3.0 | 6.96 | 92.7 | 6.83 | 90.9 |
| 2.0 | 7.57 | 100.8 | 6.71 | 89.4 |
| 1.5 | 7.59 | 101.1 | 6.82 | 90.8 |
| 1.0 | 7.33 | 97.7 | 6.68 | 89.0 |
| 0.8 | 6.79 | 90.4 | 7.03 | 93.7 |
| 0.6 | 7.24 | 96.4 | 7.13 | 95.0 |
| 0.4 | 7.31 | 97.4 | 6.97 | 92.8 |
| 0.2 | 7.32 | 97.5 | 7.22 | 96.2 |
| 0.1 | 7.78 | 103.7 | ND | ND |

ND*—not determined.

The data shows that pre-incubation with heparinase I at concentrations of 5 and 10 U/mL fully reversed the inhibitory effect of heparin on the ROX FXIa Chromogenic Assay independent from heparin concentration up to 3 IU/mL assay.

These data confirmed that the inhibitory influence of heparin on the ROX FXIa Chromogenic Assay was fully reverted by pre-treatment with heparinase I. Both concentrations of heparinase I were similarly effective and were therefore used for the analysis of the final products of the DDCPP conformance lots with the heparin-insensitive ROX FXIa Chromogenic Assay.

Example 6—Measurement of the Final Products of the DDCPP Conformance Lots with the ROX FXIa Chromogenic Assay The four final products of the DDCPP conformance lots (A, B, C and D) were measured with the ROX FXIa Chromogenic Assay, using the qualified standard method and the developed heparin-insensitive method, obtained by pretreatment with heparinase I (see Table 7). For the established FXIa Rossix assay, the four final product samples were spiked with FXIa (7.5 mIU/mL) and the recovery was determined (given in the column "Recovery %"). The developed heparin-insensitive assay was carried out using pre-treatment with 5 and 10 U heparinase/mL. The efficacy of the heparin degradation was checked by the addition of 1 IU heparin/mL to FXIa-spiked GGL. These data are shown in the column "Efficacy", where the FXIa concentrations determined in the heparin-containing FXIa-spiked sample are expressed as percentage of the expected FXIa concentration.

TABLE 7

FXIa Rossix data for the DDCPP conformance lots

| Lot No | Standard Rossix FXIa Assay: Neat sample FXIa (mIU/mL) | Standard Rossix FXIa Assay: Recovery of FXIa spiked (%) | Developed Rossix Assay: Neat sample FXIa (mIU/mL) | Developed Rossix Assay: Efficacy in heparin-spiked sample (%) |
|---|---|---|---|---|
| A | 0.43 | 105.0 | 0.36[a)] | 103.4 |
| B | <0.31 | 100.2 | <0.31[a)] | 110.8 |
| C | 0.33 | 104.2 | 0.35[b)] | 106.5 |
| D | <0.31 | 111.0 | <0.31[b)] | 101.0 |

Remark:
[a)]Heparinase pre-treatment was carried out using 5 U heparinase.
[b)]Heparinase pre-treatment was carried out using 10 U heparinase.

Both the established ROX FXIa Chromogenic assay and the developed heparin-insensitive ROX FXIa Chromogenic assay with the heparinase pre-treatment provided almost identical FXIa concentrations for the neat GGL samples, the small differences detected for two samples reflect the assay variability close to the assay's limit of quantification. FXIa spiked to the four final product samples was recovered between 100.2% and 111.0%, when the established FXIa Rossix method was used. These data indirectly proof the absence of heparin carry over from upstream intermediates into the final product. Finally, the efficacy of the heparinase pre-treatment was confirmed by the analysis of FXIa-spiked final product samples to which 1 IU/mL heparin was added. The applied heparinase I pretreatment was shown to result in full removal of the inhibitory effect of heparin and close to 100% recovery of the FXIa spiked. Heparinase I, added at 5 and 10 U/mL, showed no effects on the performance of the ROX FXIa Chromogenic assay as shown by the acceptable FXIa recoveries determined for the spiked samples. Furthermore, three of these samples were measured in six repetitions in one run to define the intra-run precision: the RSDs obtained ranged from 6.6% to 7.1%. These recovery and precision data demonstrated that the heparinase pretreatment does not change the performance of the ROX FXIa Chromogenic assay and thus allow a successful assay qualification or validation.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to readily ascertain, using no more than routine experimentation, numerous equivalents to the specific embodiments described specifically herein. Such equivalents are intended to be encompassed in the scope of the following claims.

All publications, patents, and patent applications cited herein are hereby incorporated by reference in their entirety for all purposes.

What is claimed is:

1. A method of detecting and/or quantifying Factor XIa (FXIa) in a plasma sample containing heparin, comprising:

a) incubating the plasma sample containing heparin with heparinase, essentially eliminating any heparin-dependent inhibition therein, thereby producing a heparin-depleted sample;

b) adding a defined amount of Factor IX (FIX) to the heparin-depleted sample and incubating the sample, thereby converting Factor IX to Factor IXa;

c) adding a defined amount of Factor X (FX) to the sample and incubating the sample, thereby activating Factor Xa in the sample; and d) detecting and/or quantitating FXIa in the sample by measuring activity of Factor Xa in the heparin-depleted sample.

2. The method of claim 1, wherein the heparinase comprises at least a member selected from the group consisting of heparinase, I, heparinase II, and heparinase III.

3. The method of claim 1, wherein the plasma sample comprises an IgG derived from plasma or plasma fractions.

4. The method of claim 1, wherein the plasma sample comprises an IgG derived from cryo-poor plasma.

5. The method of claim 1, wherein the plasma sample comprises an IgG derived from a plasma supernatant after C1-esterase inhibitor adsorption of cryo-poor plasma.

6. The method of claim 1, wherein the plasma sample comprises an IgG derived from a double-depleted cryo-poor plasma (DDCPP).

7. The method of claim 1, wherein the heparin is present in the sample at a concentration of at least about 0.1 IU heparin/mL of sample.

8. The method of claim 1, wherein the heparin is present in the sample at a concentration of from about 0.1 IU heparin/mL of sample to about 10 IU heparin/mL of sample.

9. The method of claim 8, wherein the heparin is present in the sample at a concentration of from about 0.1 IU heparin/mL of sample to about 3 IU heparin/mL of sample.

10. The method of claim 9, wherein the heparin is present in the sample at a concentration of about 1 IU heparin/mL of sample.

11. The method of claim 1, wherein the heparinase is present in the plasma sample of a) at a concentration of from about 0.1 U heparinase/mL of sample to about 10 U heparinase/mL of sample.

12. The method of claim 11, wherein the heparinase is present in the plasma sample of a) at a concentration of about 0.2 U heparinase/mL.

13. The method of claim 11, wherein the heparinase is present in the plasma sample of a) at a concentration of about 5 U heparinase/mL.

14. The method of claim 11, wherein the heparinase is present in the plasma sample of a) at concentration of about 10 U heparinase/mL.

15. The method of claim 1, wherein the heparin and heparinase are in a ratio from about 1 IU:0.01 U to about 1 IU:1 U.

16. The method of claim 1, wherein the sample is incubated with the heparinase for between about 5 to about 7200 seconds.

17. The method of claim 16, wherein the sample is incubated with the heparinase for about 300 seconds.

18. The method of claim 16, wherein the sample is incubated with the heparinase for about 7200 seconds.

19. The method of claim 1, wherein the sample is incubated at a temperature from about 20° C. to about 40° C.

20. The method of claim 19, wherein the sample is incubated at a temperature from about 20° C. to about 30° C.

21. The method of claim 19, wherein the sample is incubated at a temperature of about 37° C.

22. The method of claim 1, wherein the heparin-depleted sample is essentially free of heparin following a).

* * * * *